(12) United States Patent
Dassa

(10) Patent No.: US 6,730,071 B1
(45) Date of Patent: May 4, 2004

(54) COLLECTION, STORAGE, TRANSPORTATION AND SAMPLING SYSTEM AND METHOD OF USE THEREOF

(76) Inventor: Alyssa J. Dassa, 151 Beech Ter., Wayne, NJ (US) 07470

( * ) Notice: Subject to any disclaimer, the term of this patent is extended or adjusted under 35 U.S.C. 154(b) by 204 days.

(21) Appl. No.: 09/669,043

(22) Filed: Sep. 25, 2000

(51) Int. Cl.[7] .......................... A61B 19/00; A61B 5/00; B65D 33/16; B65D 30/24
(52) U.S. Cl. ...................... 604/408; 604/411; 604/415; 600/576; 600/577; 600/580; 600/581; 128/DIG. 24; 383/42; 383/47; 383/904
(58) Field of Search .............................. 604/4.01, 6.16, 604/403, 408, 409–415, 905; 600/573, 576–579, 580–581; 220/200; 222/541.1, 541.6; 128/DIG. 24; 383/200, 202–203, 42, 43, 44, 47, 48, 49, 61.1, 121, 127, 904

(56) References Cited

U.S. PATENT DOCUMENTS

| | | | |
|---|---|---|---|
| 989,885 A | * 4/1911 | Tillison | 137/447 |
| 4,303,067 A | * 12/1981 | Connolly et al. | 604/408 |
| 4,561,110 A | 12/1985 | Herbert | 604/408 |
| 4,655,764 A | 4/1987 | Sato | 604/408 |
| 4,759,756 A | * 7/1988 | Forman et al. | 604/413 |
| 4,943,283 A | 7/1990 | Hogan | 604/198 |
| 5,122,129 A | 6/1992 | Olson et al. | 604/905 |
| 5,342,345 A | 8/1994 | Spencer | 604/408 |
| 5,460,625 A | 10/1995 | Johnson | 604/403 |
| 5,496,301 A | 3/1996 | Hlavinka et al. | 604/409 |
| 5,578,028 A | 11/1996 | Drago et al. | 604/408 |
| 5,658,271 A | 8/1997 | Loubser | 604/410 |
| 5,685,875 A | 11/1997 | Hlavinka et al. | 604/409 |
| 5,779,693 A | 7/1998 | Ropiak et al. | 604/408 |
| 6,039,718 A | 3/2000 | Niedospial, Jr. | 604/408 |
| 6,328,726 B1 | * 12/2001 | Ishida et al. | 604/408 |

FOREIGN PATENT DOCUMENTS

EP  0 916 307 A1  *  5/1999
EP  1 190 673 A1  *  3/2002

* cited by examiner

*Primary Examiner*—Patricia Bianco
(74) *Attorney, Agent, or Firm*—Nanette S. Thomas, Esq.; Scott J. Rittman, Esq.

(57) ABSTRACT

A blood collection bag assembly is provided. The assembly includes a flexible blood collection bag, a length of flexible tubing extending from and communicating with the bag and a connector secured to the end of the flexible tubing remote from the bag. The connector includes a needle pierceable resealable closure secured in sealing engagement with the end of the flexible tubing remote from the bag. The connector can be used with a conventional needle holder, such as the type used to collect specimens of blood into an evacuated tube. The blood collection bag assembly has no sharp components, and hence is safe and easy to use. Additionally, the blood collection bag assembly can be used with conventional evacuated tubes to avoid cut and drip techniques for collecting specimens of blood for analysis.

5 Claims, 3 Drawing Sheets

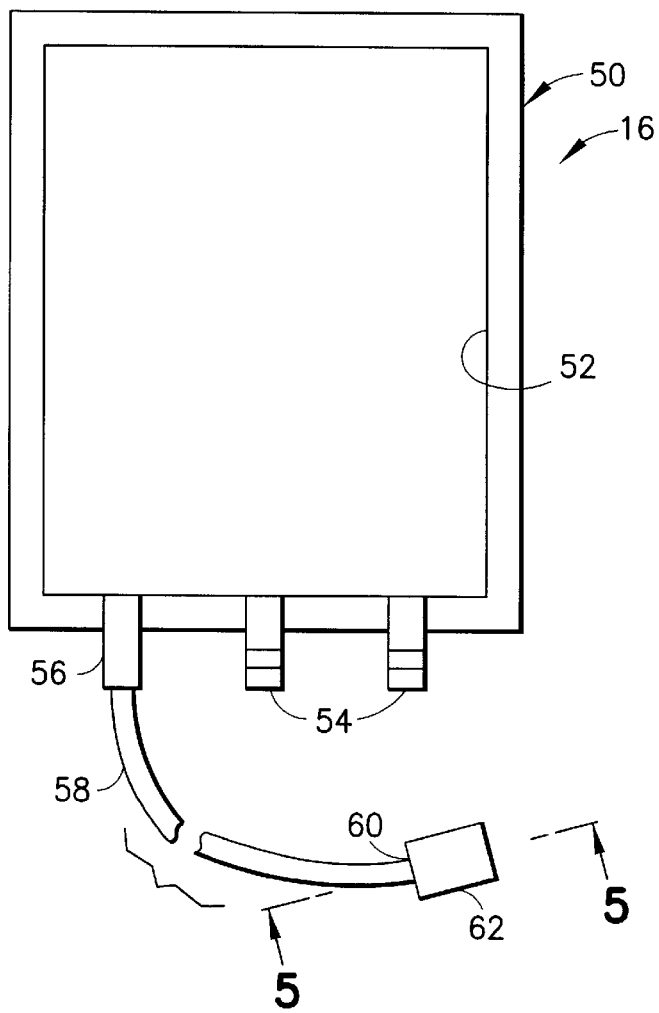
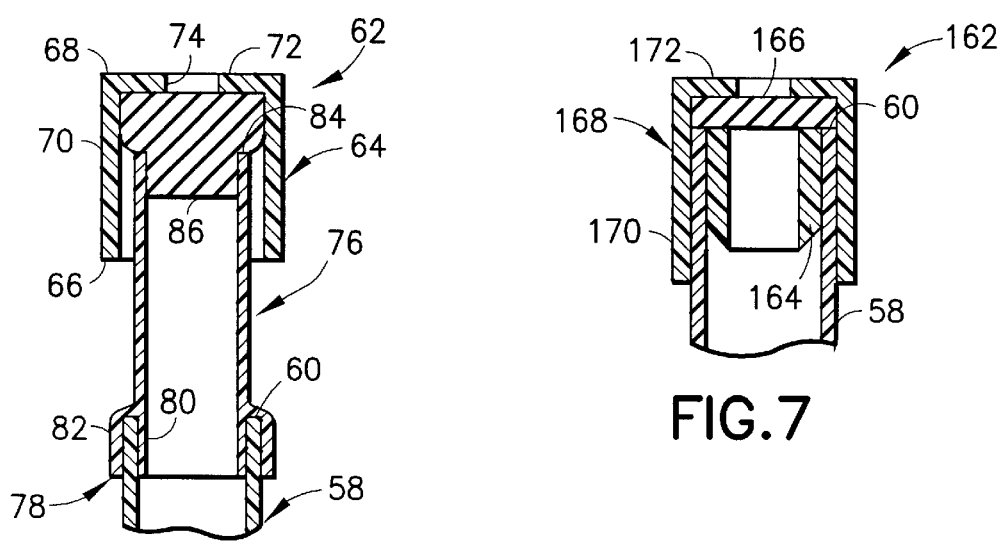

COLLECTION, STORAGE, TRANSPORTATION AND SAMPLING SYSTEM AND METHOD OF USE THEREOF

BACKGROUND OF THE INVENTION

1. Field of the Invention

The present invention relates to a collection, storage, transporting and sampling system for fluids and method of use thereof. More particularly, the present invention relates to a system and method for collecting, storing, transporting and sampling blood.

2. Description of the Related Art

A conventional blood collection bag assembly includes a bag pre-filled with an anticoagulant solution and a length of plastic tubing extending therefrom with a needle mounted to the end of the tubing remote from the bag. The bag is used to collect blood or donated blood for medical use.

Medical professionals will employ a "cut and drip technique" or a "stab" technique to collect a small sample of the donated blood for laboratory analysis to assure safety of the blood in the bag and to identify characteristics of the blood such as ABO group and the Rh type. These techniques allow the medical professional to collect a sample from the bag while maintaining the integrity and sterility of the bag and blood sample.

To perform the "cut and drip" technique with a blood bag, any packaging cover that had been mounted to the needle is removed, and the pointed distal end of the needle is inserted into a blood vessel of the patient or donor to generate a flow of blood through the tubing and into the bag. After a sufficient volume of blood has been collected, the tubing is clamped at two locations to prevent further flow of blood. The tubing then is cut or separated between the clamps. The removal of the clamp closest to the bag causes blood in the severed section of tubing to flow into the bag. The cut section of tube then is recapped, and the blood bag is stored and/or used. The clamp then is removed from the remaining section of tubing. Blood that had remained in the tubing between the clamp and the needle is enabled to flow into one or more blood collection tubes. The blood collection tubes then are sealed, labeled and shipped to a laboratory for analysis. The needle is removed from the patient and discarded along with the section of tubing connected thereto.

Blood collection bag assemblies that have the cut and drip technique have the presence of the needle on the end of the tubing remote from the blood collection bag which may create a risk to the donor, patient and medical professional. Additionally, the above-described assembly is in communication with the ambient environment for at least a short period of time. Hence, the potential exists for contamination of the interior of the blood collection bag, and such contamination can affect the safety and utility of the entire assembly. Similarly, the cut and drip technique requires the specimen collection tube to be in communication with the ambient environment as the open system is used to deposit a small sample of blood into the specimen collection tube for subsequent analysis. Furthermore, the blood sample collected for laboratory analysis may be mixed with the contents of the blood bag such as an anticoagulant, which may affect the test results. The technician performing such a blood collection process must perform a large number of steps in a specified order and often using a specific system of tools for clamping and cutting the flexible tubing and for subsequently collecting and then sealing the containers of blood.

In blood banking procedures, there are a number of tests that are conducted on the unit of blood to assure safety to the recipient of the unit of blood. Such tests include cross matching and type testing. To carry out these tests, while maintaining the closed system of the unit of blood, the blood bank technician breaks off a blood filled segment of tubing that is attached to the unit of blood. This technique is complex for the user.

Therefore, there exists a need to provide a collection assembly or kit that: (i) provides a simple and closed system in which interior portions of a blood collection bag are not exposed to ambient conditions; (ii) provides no chance for contamination of the blood collection bag or to the blood sample collected therein; (iii) avoids the complexities and costs associated with cut and drip techniques or valves and adapters; (iv) provides for collecting directly from the blood bag without use of segments; and (v) provides for various medical devices to be easily connected or linked with the present invention.

SUMMARY OF THE INVENTION

The present invention is to a blood collection assembly comprising a blood collection bag, flexible tubing extending from and communicating with the blood collection bag and a closed needle pierceable connector or interlock connector mounted to the end of the flexible tubing remote from the blood collection bag.

Desirably, the connector may include a substantially cylindrical cap that surrounds a portion of the flexible tubing that extends remotely from the blood collection bag. The cap may include an annular end wall extending over a portion of the flexible tube and having a central aperture aligned with the passage through the flexible tubing. A needle pierceable seal may be disposed between the annular end wall of the cap and the end of the flexible tubing. Additionally, the connector may include an inner fitting disposed within the flexible tubing to prevent the flexible tubing from collapsing out of engagement with the cylindrical sidewall of the cap. In addition, the connector may further include a locking mechanism that maintains the connection between the cap and other components. Other components that could be connected to the cap would have a mating connector that would be dimensioned to temporarily attach or lock to the cap.

The connector may be used with a needle holder that enables access to a blood vessel. The needle holder includes a widely open proximal end, a partly closed distal end and a generally cylindrical sidewall extending between the ends. The distal end may have an inwardly extending annular wall which defines a central opening with structure for engaging a needle assembly. For example, the opening in the annular distal end wall of the needle holder may include an array of internal threads. The needle assembly may include a double ended needle cannula having a pointed distal end for venipuncture and an opposed pointed proximal end. The needle assembly may further include a hub mounted to the needle cannula between the ends. The hub may be configured for engagement with the aperture in the annular distal end wall of the needle holder. The needle assembly may further include a multiple specimen sleeve mounted over the proximal end of the needle cannula. The cylindrical sidewall of the needle holder may define an inside diameter selected for slidably receiving a conventional evacuated blood specimen collection tube. Additionally, the cylindrical sidewall of the needle holder defines an inside diameter that is dimensioned to slidably receive the connector mounted to the end of the flexible tube remote from the blood collection bag.

The assembly of the present invention can be used by mounting the needle assembly to the needle holder such that the proximal end of the needle cannula extends into the needle holder. The distal end of the needle cannula may be placed in communication with a blood vessel of a patient in a conventional manner. Blood flow from the proximal end of the needle cannula is impeded by the multiple specimen collection sleeve mounted over the proximal end of the needle cannula and disposed within the needle holder. The blood collection process may continue by slidably inserting one or more evacuated blood specimen collection tubes into the open end of the needle holder such that the needle pierceable septum over the end of the evacuated blood specimen collection tube engages the multiple specimen sleeve of the needle cannula. Forces exerted by the evacuated blood specimen collection tube will cause the pointed proximal end of the needle cannula to pierce through the multiple specimen sleeve and subsequently to pierce through the rubber stopper or septum that sealingly covers the evacuated blood specimen collection tube. The evacuated conditions within the tube will cause a flow of blood from the patient through the needle cannula and into the evacuated blood specimen collection tube. Upon collection of a selected volume of blood for analysis, the evacuated blood specimen collection tube is slidably removed from the needle holder. The septum or other such seal across the open end of the evacuated blood specimen collection tube will reseal and the multiple specimen sleeve over the proximal end of the needle cannula will expand longitudinally and reseal over the proximal end of the needle cannula. At least one additional specimen of blood can be collected in additional evacuated blood specimen collection tubes.

After a sufficient number of specimens of blood have been collected for analysis, the connector of the blood bag assembly is urged into the open end of the needle holder and locked into position. The stopper or septum covering the end of the blood collection tube remote from the blood collection bag causes a displacement of the multiple specimen collection sleeve, as had occurred with the evacuated blood specimen collection tubes. As a result, the pointed proximal end of the needle cannula will pierce through the multiple specimen sleeve and subsequently will pass through the stopper extending across the end of the flexible tubing remote from the blood collection bag. A selected volume of blood from the donor will flow through the needle cannula, into the flexible tubing and subsequently into the blood collection bag by gravity. Upon collection of a sufficient volume of blood, the connector merely is slidably removed from the needle holder. The seal over the end of the tube remote from the blood collection bag will reseal, and the multiple specimen collection sleeve will expand longitudinally and seal over the proximal end of the needle cannula to prevent a further flow of blood from the patient. The needle holder and the needle assembly connected thereto then are removed from the patient and shielded in a selected conventional manner.

A significant advantage of the assembly of the present invention is that it provides a closed system in which interior portions of the blood collection bag are not exposed to ambient conditions. Thus, there is no chance for contamination to the interior of the blood collection bag or to the blood sample collected therein.

Furthermore, the assembly avoids the complexities and costs associated with the cut and drip techniques or valves and adapters.

A notable advantage of the present invention is that during the blood banking process, sterile samples may be collected directly from the blood bag. This eliminates the use of segments and simplifies the process.

Another notable advantage of the present invention is that blood filters, infusion catheters, testing cartridges, test tubes and other medical devices can be linked with the assembly of the present invention by the connector or interlock which improves safety to the user.

DESCRIPTION OF THE DRAWINGS

FIG. 4 is a front elevational view of the blood bag assembly of the kit.

FIG. 5 is a cross-sectional view taken along line 5—5 in FIG. 4.

FIG. 7 is a cross-sectional view similar to FIG. 5 but showing an alternate connector.

DETAILED DESCRIPTION

Figure 1:
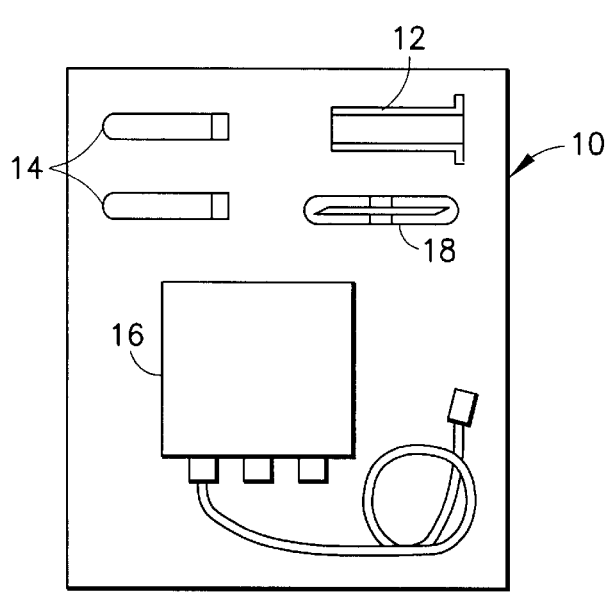
FIG. 1 is a top plan view of a blood donation kit in accordance with the subject invention.

A kit in accordance with the present invention is identified by the numeral 10 in FIG. 1. Kit 10 includes a needle holder 12, a plurality of evacuated specimen collection tubes 14, a blood bag assembly 16 and a needle assembly 18. As shown in FIG. 1, kit 10 is schematically illustrated as a single package. However, kit 10 may include two separate or separable packages. A first package of kit 10 may include needle holder 12 and blood collection tube 14. A second package of kit 10 may include blood bag assembly 16. The provision of two separate parts for kit 10 enable the careful matching of specimen collection tubes 14 with the needs of a particular medical procedure. For example, more or fewer evacuated specimen collection tubes 14 may be provided, and certain of the evacuated specimen collection tubes 14 may have additives therein in accordance with the laboratory analysis to be performed on collected specimens.

Figure 2:
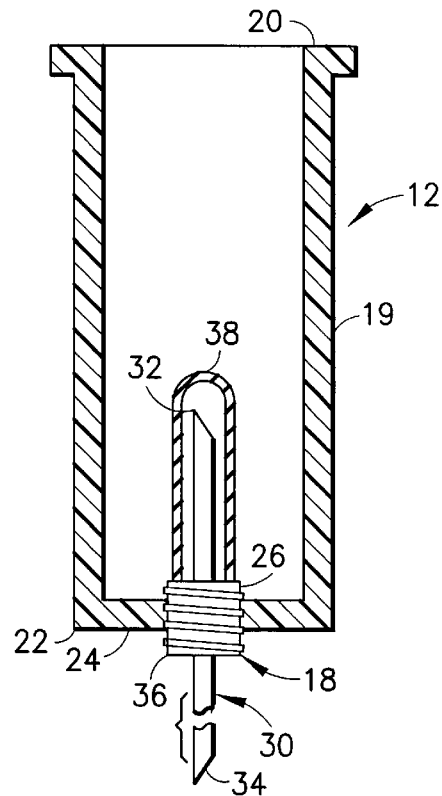
FIG. 2 is a longitudinal cross-sectional view of a prior art needle holder that is part of the kit of FIG. 1.
Figure 3:
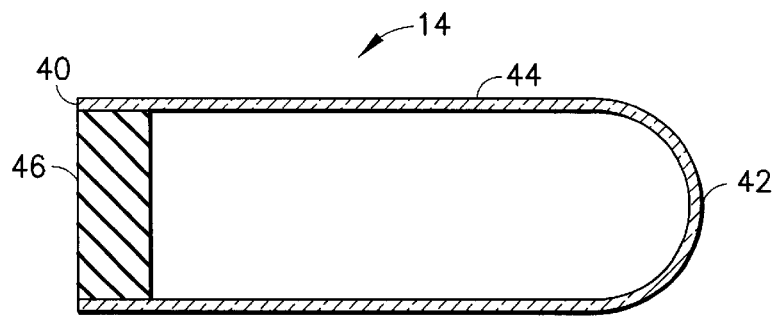
FIG. 3 is a longitudinal cross-section view of a prior art evacuated tube from the kit of FIG. 1.

Needle holder 12 is shown more clearly in FIG. 2 and may be a prior art structure. As shown most clearly in FIG. 2, needle holder 12 has a substantially cylindrical sidewall 19 that extends from an open proximal end 20 of needle holder 12 to a distal end 22. An annular distal end wall 24 extends inwardly from cylindrical sidewall 19 and is provided with an internally threaded central aperture 26. Needle assembly 18 is releasably engaged in aperture 26 of needle holder 12. Needle assembly 18 includes an elongate needle cannula 30 having a pointed proximal end 32, a pointed distal end 34 and a lumen extending therebetween. An externally threaded plastic hub 36 is mounted to needle cannula 30 between proximal and distal ends 32 and 34. Hub 36 is threadedly engaged in aperture 26 of annular distal end wall 24. Needle assembly 30 further includes a multiple specimen sleeve 38 covering proximal end 32 of needle cannula 30. Sleeve 38 is collapsible in a distal direction in response to distal forces exerted thereon. Additionally, sleeve 38 is readily pierceable by pointed proximal end 32 of needle cannula 30 to enable communication between the lumen of needle cannula 30 and the portions of needle holder 12 within the cylindrical sidewall 18 thereof. Upon release of forces thereon, sleeve 38 will resiliently return to its non-collapsed condition and into sealing disposition around proximal end 32 of needle cannula 30.

Needle holder 12 is used sequentially with evacuated specimen collection tubes 14. Each evacuated tube 14 includes an open proximal end 40, a closed bottom end 42 and a rigid cylindrical sidewall 44 extending therebetween. Sidewall 44 has an outside diameter sufficiently small to permit evacuated tube 14 to be slidably inserted into open proximal end 20 of sidewall 18 on needle holder 12. Evacuated tube 14 further includes a closure 46 sealingly engaged with sidewall 44 at open end 40. Closure 46 is formed from a needle pierceable resealable material that will retain vacuum conditions in tube 14.

Needle holder 12 and evacuated tube 14 are used substantially in a conventional manner by first placing pointed distal end 34 of needle 30 in communication with a selected blood vessel of a patient. Sleeve 38 over proximal end 32 of needle cannula 30 will prevent an outflow of blood. Evacuated tube 14 then is inserted slidably into needle holder 12 such that closure 46 on evacuated tube 14 engages and collapses sleeve 38. Sufficient movement of evacuated tube 14 causes pointed proximal end 32 of needle cannula 30 to pierce sleeve 38 and to pierce closure 46. Thus, the evacuated interior of tube 14 is placed in communication with the lumen through needle cannula 30. Vacuum conditions within tube 14 generate a flow of blood into tube 14. After a sufficient volume of blood has been collected in tube 14, the medical technician merely pulls tube 14 proximally and out of needle holder 12. Closure 46 on evacuated tube 14 will reseal after separation from needle cannula 30. Additionally, sleeve 38 will resiliently expand and reseal to enclose proximal end 32 of needle cannula 30. One or more additional evacuated tubes 14 similarly may be employed with needle holder 12 to obtain additional specimens. The collected specimens are labeled and sent to a laboratory for subsequent analysis.

Blood bag assembly 16 of kit 10 is used with needle holder 12. In particular, as shown in FIG. 4, blood bag assembly 16 includes a flexible plastic bag 50 having an enclosed blood reservoir 52 defined therein. Bag 50 further includes at least one access port 54 that provides communication with reservoir 52. However, access ports 54 are heat sealed to maintain sterility of reservoir 52 within bag 50. The heat seal of access ports 54 enables the plastic material of bag 50 to be peeled open at access ports 54 for accessing blood collected in bag 50. Bag 50 further includes an inlet and/or outlet port 56. A length of flexible tubing 58 has one end connected to inlet port 56 and an opposed end 60 remote from inlet 56.

Blood collection bag assembly 16 further includes a connector 62 mounted to end 60 of flexible tubing 58. Connector 62 includes a cap 64 as shown most clearly in FIG. 5. Cap 64 is formed from a rigid plastic material and has a proximal end 66, a distal end 68 and a cylindrical sidewall 70 extending therebetween. Sidewall 70 has an inside diameter greater than the outside diameter of flexible tubing 58. Additionally, cylindrical sidewall 70 of cap 64 has an outside diameter that is less than the inside diameter of sidewall 19 on needle holder 12. Cap 64 further includes an annular distal end wall 72 that extends inwardly from distal end 68 of cylindrical sidewall 70. Annular distal end wall 72 includes a central aperture 74 extending therethrough.

In the embodiment shown in FIG. 5, connector 62 further includes a tubing support 76 received within cylindrical sidewall 70 of cap 64. Support 76 includes a proximal end 78 characterized by concentrically spaced inner and outer walls 80 and 82 respectively. End 60 of flexible tubing 58 is securely engaged between inner and outer walls 80 and 82 at proximal end 78 of support 76. Support 76 further includes a distal end 84. A needle pierceable resealable elastomeric stopper 86 is sealingly engaged within distal end 84 of support 76. Stopper 86 further is dimensioned to sealingly engage portions of cylindrical sidewall 70 of cap 64 adjacent annular distal end wall 72 of cap 64. Thus, stopper 86 functions to seal support 76 and tubing 58 and to frictionally retain support 76 and tubing 58 in cap 64.

Figure 6:
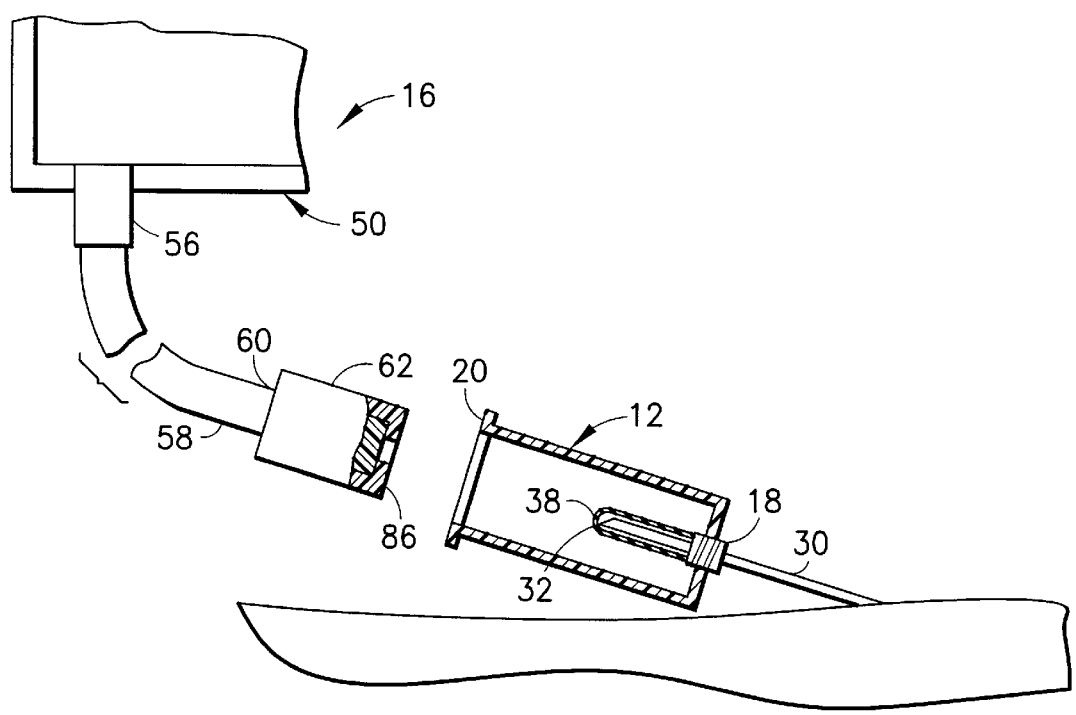
FIG. 6 is an exploded elevational view, partly in section, of the blood bag assembly in use.

Blood bag assembly 16 is used with needle holder 12 in a manner substantially similar to the above-described use of evacuated tubes 14. In particular, as shown in FIG. 6, connector 62 of blood bag assembly 16 is slidably inserted into open proximal end 20 of needle holder 12. Stopper 86 of connector 62 will substantially axially align with pointed proximal end 32 of needle cannula 30. Sleeve 38 will collapse distally in response to the distal movement of connector 62 into needle holder 12. Pointed proximal end 32 of needle cannula 30 then will pierce through stopper 86 to place needle cannula 30 in communication with flexible tube 58 and reservoir 52 of blood collection bag 50. Blood then can be collected substantially in the conventional manner for substantially filling reservoir 52. Upon collection of the specified volume of blood in reservoir 52, connector 62 is moved proximally out of needle holder 12 to separate connector 62 from needle cannula 30. In response to this separation, stopper 86 will reseal and sleeve 38 will expand and reseal around needle cannula 30. Needle cannula 30 of needle holder 12 then can be removed from the patient and shielded in an appropriate known manner to prevent accidental sticks. The collected blood in blood bag assembly 16 then can be stored and/or used as appropriate.

Blood bag assembly 16 has several significant advantages. First, blood bag assembly 16 has no sharp implement connected thereto. Hence, use of blood collection bag assembly both prior to and after collection of blood is easy and substantially risk free. Additionally, connector 62 ensures that blood collection bag assembly 16 is a closed system with little risk of contamination to interior portions of blood collection bag assembly 16. In particular, connector 16 ensures that flexible tubing 58 and reservoir 52 are substantially isolated from ambient environmental conditions both prior to use, during use and after use. Still further, connector 60 is readily dimensioned for use with the same needle holder that is used to collect specimens of blood for analysis. Hence, blood collection bag assembly 16 and connector 62 thereof are designed for use with equipment commonly employed by medical personnel.

FIG. 7 shows an alternate connector assembly 162 for use with blood collection bag assembly 16. Connector 162 has an inner fitting 164 that is slidably engaged within flexible tubing 58 adjacent end 60 thereof. A resealable stopper 166 is positioned adjacent end 60 of flexible tubing 158. Cap 168 then is mounted over closure 166 and over portions of flexible tubing 58 adjacent end 160. Cap 168 includes a cylindrical sidewall 170 within an inside diameter that is dimensioned for secure gripping engagement over portions of flexible tube 58 having inner fitting 164 therein. Thus, flexible tubing 158 effectively is squeezed between inner fitting 164 and cylindrical sidewall 170 of fitting 168. Fitting 168 further includes an annular end wall 172 that extends inwardly from cylindrical sidewall 170 and registers with end 60 of flexible tubing 58. Thus, end wall 172 tightly retains stopper 166 against end 60 of flexible tubing 58. Connector 162 can be used substantially as described above with respect to connector 62.

While the invention has been described with respect to certain preferred embodiments, it is apparent that various changes can be made without departing from the scope of the invention as defined by the appended claims. For example, the blood bag assembly may be used with other needle holders. Additionally, the needle holder described and illustrated above is not depicted with a safety shield for shielding after removal of the needle cannula from the blood vessel. However, safety shields may be provided. Additionally, the needle holder can be provided with mechanisms for safely ejecting the used needle assembly into a sharps receptacle, and to thereby enable reuse of the needle holder. As illustrated above, the blood bag assembly is shown as being packaged with a needle holder and with several evacuated specimen collection tubes. However, the blood bag assembly may be packaged and sold separately. Additionally, a blood collection method is described in which specimens of blood are collected in evacuated tubes prior to a collection of blood in the blood bag. However, this procedure may be reversed, so that specimens of blood are collected in the evacuated tubes after collecting the blood in the blood bag. These and other changes will be apparent to a person skilled in the art after having read the subject disclosure. Additionally, there are a number of other components that may be used with the connector of the present invention. Such components include, but are not limited to, winged needle sets, blood filtration products, infusion or transfusion catheters, secondary tubes and diagnostic test cartridges.

It is also within the purview of this invention, that other fluids such as urine, pleural effusions or other bodily fluids or tissues, water samples, flood samples or other environmental samples may be used in the assembly and method of the present invention.

What is claimed is:

1. A blood collection bag assembly comprising a flexible bag for collecting a volume of blood, flexible tubing extending from and communicating with the bag, the flexible tubing having an end remote from the bag, and a connector secured to said end of said flexible tubing remote from said bag, said connector comprising:
    a needle pierceable resealable closure sealingly engaged with said end of said flexible tubing,
    an inner fitting supportingly engaged within said end of said flexible tubing remote from said bag, said fitting preventing said flexible tubing from collapsing, and thereby facilitating secure engagement of said closure with said flexible tubing,
    a cap, said cap comprising a cylindrical sidewall surrounding said end of said flexible tubing and an annular end wall extending inwardly from said cylindrical sidewall, said annular end wall securely engaging said closure for sealing said flexible tubing,
    wherein the inner fitting and the cap are separate from one another, said cylindrical sidewall of said cap being forcibly engaged over said end of said flexible tubing for securely gripping said end of said flexible tubing between said cylindrical sidewall and said inner support.

2. The blood collection bag assembly of claim 1, wherein said closure has opposed parallel planar surfaces, one said surface of said closure being sealingly engaged by said annular end wall of said cap, said opposed surface of said closure being sealingly engaged against said end of said flexible tubing and against said support.

3. A blood collection bag assembly comprising a flexible bag for collecting a volume of blood, flexible tubing extending from and communicating with the bag, the flexible tubing having an end remote from the bag, and a connector secured to said end of said flexible tubing remote from said bag, said connector comprising a needle pierceable resealable closure sealingly engaged with said end of said flexible tubing, wherein the connector includes a generally tubular support, having a first end with concentric spaced apart inner and outer walls securely engaging said end of said flexible tubing therebetween, said support further having a second end, said closure being securely engaged in said second end of said support and having a portion defining a cross-section greater than the support, said connector further comprising an outer cap, said outer cap having a cylindrical wall telescoped over at least said second end of said inner support and sealingly engaged with portions of said closure, said cap of said connector further including an annular end wall extending inwardly and overlying portions of said closure.

4. A blood collection kit comprising:
    a needle holder,
    a needle assembly engageable with said needle holder, and
    a blood collection bag assembly comprising a flexible bag for collecting a volume of blood, flexible tubing extending from and communicating with the bag, the flexible tubing having an end remote from the bag, and a connector secured to said end of said flexible tubing remote from said bag, said connector comprising:
        a needle pierceable resealable closure sealingly engaged with said end of said flexible tubing,
        an inner fitting supportingly engaged within said end of said flexible tubing remote from said bag, said fitting preventing said flexible tubing from collapsing, and thereby facilitating secure engagement of said closure with said flexible tubing, and
        a cap, said cap comprising a cylindrical sidewall surrounding said end of said flexible tubing and an annular end wall extending inwardly from said cylindrical sidewall, said annular end wall securely engaging said closure for sealing said flexible tubing, and
    wherein the inner fitting and the cap are separate from one another, said cylindrical sidewall of said cap being forcibly engaged over said end of said flexible tubing for securely gripping said end of said flexible tubing between said cylindrical sidewall and said inner support.

5. A blood collection kit comprising:
    a needle holder,
    a needle assembly engageable with said needle holder,
    a blood collection bag assembly comprising a flexible bag for collecting a volume of blood, flexible tubing extending from and communicating with the bag, the flexible tubing having an end remote from the bag, and a connector secured to said end of said flexible tubing remote from said bag, said connector comprising a needle pierceable resealable closure sealingly engaged with said end of said flexible tubing, wherein the connector includes a generally tubular support, having a first end with concentric spaced apart inner and outer walls securely engaging said end of said flexible tubing therebetween, said support further having a second end, said closure being securely engaged in said second end of said support and having a portion defining a cross-section greater than the support, said connector further comprising an outer cap, said outer cap having a cylindrical wall telescoped over at least said second end of said inner support and sealingly engaged with portions of said closure, said cap of said connector further including an annular end wall extending inwardly and overlying portions of said closure.

* * * * *